United States Patent [19]

Varady et al.

[11] Patent Number: 5,417,863

[45] Date of Patent: May 23, 1995

[54] QUANTITATIVE MEASUREMENT OF LDL

[75] Inventors: Laszlo Varady, Malden; Noubar B. Afeyan, Brookline; Robert Langer, Newton; Shmuel Shefer, Brookline, all of Mass.

[73] Assignee: PerSeptive Biosystems, Inc., Cambridge, Mass.

[21] Appl. No.: 269,952

[22] Filed: Jun. 30, 1994

Related U.S. Application Data

[63] Continuation of Ser. No. 950,454, Sep. 24, 1992, abandoned.

[51] Int. Cl.$^6$ ............................................. B01D 15/08
[52] U.S. Cl. .................................. 210/635; 210/656; 210/198.2; 436/71; 436/161; 436/178; 530/413; 530/416
[58] Field of Search ..................... 436/71, 161, 178; 530/413, 416; 210/635, 656, 198.2

[56] References Cited

U.S. PATENT DOCUMENTS

| | | | |
|---|---|---|---|
| 4,096,136 | 6/1978 | Ayers | 436/71 |
| 4,110,077 | 8/1978 | Klein | 436/71 |
| 4,147,606 | 4/1979 | Golias | 436/71 |
| 4,167,467 | 9/1979 | Golias | 436/71 |
| 4,185,963 | 1/1980 | Heuck | 436/71 |
| 4,290,774 | 9/1981 | Girgis | 210/71 |
| 4,309,188 | 1/1982 | Bentzen | 530/413 |
| 4,366,244 | 12/1982 | Pascal | 435/11 |
| 4,569,917 | 2/1986 | Maier | 436/178 |
| 4,603,010 | 7/1986 | Ayers et al. | 424/101 |
| 4,828,986 | 5/1989 | Smith | 436/518 |
| 4,883,765 | 11/1989 | Tamir | 436/71 |
| 4,900,680 | 2/1990 | Miyazawa | 436/71 |
| 4,933,844 | 6/1990 | Otovos | 436/71 |
| 5,019,270 | 5/1991 | Afeyan | 210/656 |
| 5,078,853 | 1/1992 | Manning | 436/71 |
| 5,141,872 | 8/1992 | Tamir | 436/71 |

FOREIGN PATENT DOCUMENTS

| | | | |
|---|---|---|---|
| 0165709 | 12/1985 | European Pat. Off. | 210/198.2 |
| 3925876 | 2/1991 | Germany | 436/71 |
| 60-97271 | 5/1985 | Japan | 436/71 |
| 63-243878 | 10/1988 | Japan | 436/71 |
| 1091066 | 5/1984 | U.S.S.R. | 436/71 |
| WO8905458 | 6/1989 | WIPO | 436/71 |

OTHER PUBLICATIONS

Afeyan, Perfusion Chromatography—An Approach to Purifying Biomolecules, Bio/Technology vol. 8, Mar. 1990 pp. 203–206.

Snyder, Introduction to Modern Liquid Chromatography John Wiley & Sons, Inc., New York, 1979, pp. 135–139, 204–206, & 560–565.

Bentzen, "Direct Determination of Lipoprotein Distribution with Micro—Scale Affinity Chromatography Columns", Clin. Chem 2817, pp. 1451–1456 (1982).

Deutscher, "Guide to Protein Purification," Methods in Enzymology, vol. 182, Academic Press, Inc, San Diego, 1990 pp. 309–310 & 317–318.

Albers et al., "Evaluation of a monoclonal antibody–based enzyme–linked immunosorbent assay as a candidate reference method for the measurement of apolipoprotein B–100," *J. Lipid Research*, 30:1445 (1989).

(List continued on next page.)

*Primary Examiner*—Ernest G. Therkorn
*Attorney, Agent, or Firm*—Testa, Hurwitz & Thibeault

[57] ABSTRACT

Disclosed is a method for the rapid quantitative determination of low density lipoprotein (LDL) in a biological fluid sample containing LDL, very low density lipoprotein (VLDL) and high density lipoprotein (HDL). The sample is first passed through a matrix to bind LDL to the matrix. The LDL is then eluted from the matrix differentially from VLDL and HDL. A parameter representative of the concentration of a solute exiting the matrix during the interval when LDL is eluted is then determined, wherein the parameter is proportional to the amount of the LDL in the sample. The parameter may be determined, e.g., by electronically integrating under a spectrophotometrically detected peak of eluted LDL.

15 Claims, 9 Drawing Sheets

OTHER PUBLICATIONS

Chapman, "Plasma Lipoproteins," *Methods in Enzymology*, 128:70–143 (1986).

Friedwald et al., "Estimation of the Concentration of Low-Density Lipoprotein Cholesterol in Plasma, Without Use of the Preparative Ultracentrifuge," *Clinical Chemistry*, 18:499–502 (1972).

McNamara et al., "Effect of Gender, Age, and Lipid Status on Low Density Lipoprotein Subfraction Distribution," *Arteriosclerosis*, 7:483–490 (1987).

Otvos et al., "Evaluation of the Clinical Utility of Plasma Lipoprotein Levels Derived by Proton NMR Spectroscopy," (Abstract) AACC Annual Meeting, Washington, D.C., Jul., 1991, *Clin. Chem.*, 37:918–919 (1991).

Rudel et al., "Characterization of Plasma Lipoproteins Separated and Purified by Agarose-Column Chromatography," *Biochem. Journal*, 139:89–95 (1974).

Warnick et al., "Estimating Low-Density Lipoprotein Cholesterol by the Friedewald Equation is Adequate for Classifying Patients on the Basis of Nationally Recommended Cutpoints," *Clinical Chemistry*, 36:15–19 (1990).

Wieland and Seidel, "A Simple Specific Method for Precipitation of Low Density Lipoproteins," *J. of Lipid Research*, 24:904–909 (1983).

Williams et al., "Rapid Method for Measuring Plasma Low-Density Lipoprotein Turnover Using High-Performance Gel Exclusion Chromatography," *J. Chromatography*, 375:233–245 (1986).

QUANTITATIVE MEASUREMENT OF LDL

This is a continuation of application Ser. No. 07/950,454, filed on Sep. 24, 1992, now abandoned.

BACKGROUND OF THE INVENTION

This invention relates to methods for determining the concentration of low density lipoprotein (LDL) in a plasma sample.

Elevated low density lipoprotein (LDL) cholesterol (LDL-C) levels have been linked directly with premature coronary heart disease (CHD). Grundy, S., *JAMA*, 264:3053 (1990). Many studies have shown that LDL-C lowering drugs or diets can reduce CHD. The atherogenic properties of LDL have been the subject of detailed investigation. Steinberg et al., *JAMA*, 264:3047 (1990). The National Cholesterol Education Program (NCEP) has set guidelines for the treatment of high blood cholesterol in adults over 20 years of age. Report of the NCEP Expert Panel in Detection, Evaluation and Treatment of High Blood Cholesterol in Adults, *Arch. Intern. Med.*, 148:36 (1988).

The current clinical practice requires the measurement of triglycerides (TG), high density lipoprotein (HDL) and LDL, only if total cholesterol (TC) is at least in the borderline risk category ($\geq 200$ mg/dL) and the patient has two or more CHD risk factors. The desirable level of LDL-C is $<130$ mg/dL. The borderline high risk level of LDL-C for CHD is 130–159 mg/dL. The high risk level of LDL-C for CHD is $\geq 160$ mg/dL. The 75th percentile for middle aged Americans corresponds to an LDL-C level of 160 mg/dL, also the level demarking the level of high risk for CHD. N. Rifai and R. Warnick, eds., *Lipid and Lipoprotein Risk Factors*, AAAC press, 1991.

Lipoproteins are metabolized according to a complex pathway. N. Rifai and R. Warnick, eds., *Lipid and lipoprotein Risk Factors*, AAAC press, 1991. Fats are absorbed in the intestine and are packaged into large triglyceride-rich particles (chylomicrons)o These are broken down into components including HDL which is taken up by the liver. The liver synthesizes very low density lipoprotein (VLDL) which is broken down into LDL. LDL is defined on a density basis of 1.006–1.063 kg/L by ultracentrifugation. LDL includes a hydrophobic lipid core of cholesterol esters and triglyceride surrounded by a coat of phospholipid, unesterified cholesterol and apolipoproteins (Apo B-100, Apo CIII and Apo E). On an average weight basis, LDL comprises 38% cholesterol ester, 22% phospholipid, 21% protein, 11% TG and 8% unesterified cholesterol. Chapman, J., *Methods in Enzymology*, 128:70 (1986). LDL is the major cholesterol carrying lipoprotein in plasma. The central role of LDL in cholesterol processing and its association with CHD has led the NCEP to recommend that LDL-C be used by physicians in determining patient treatment for hypercholesterolemia. This places increased emphasis on the accuracy and reliability of such measurements.

Many techniques are available for the measurement of total cholesterol, as well as individual lipoproteins. These vary in specificity, clinical prevalence, automation, simplicity and speed. Total cholesterol may be measured enzymatically. Cholesterol esterase is first used to hydrolyze the esters. Then cholesterol oxidase converts cholesterol to cholestenone and hydrogen peroxide. Finally, peroxidase is used to convert a chromogen, in the presence of the peroxide, into a dye which can absorb light in the visible wavelength range. The intensity of the color produced is directly proportional to the total cholesterol concentration in the sample. Automated instruments are available which perform this measurement clinically, e.g.: Refrotron ™ (Boehringer Manheim Diagnostics, Indianapolis, Ind.); Kodak DT 6D ™ (Eastman Kodak, Rochester, N.Y.); and Abbott Vision ™ (Abbott Laboratories, North Chicago, Ill.).

High density lipoprotein (HDL) cholesterol measurements are performed after the separation of HDL from the rest of serum lipoproteins. This can be accomplished by ultracentrifugation at 1.063 kg/L (18 hrs, 10° C., at 40,000 rpm). Alternatively, electrophoretic separation on polyacrylamide or agarose gel can be used, but only for qualitative analysis.

Selective chemical precipitation is commonly used in clinical laboratories, wherein reagents such as heparin-manganese chloride, dextran sulfate-magnesium chloride or polyethylene glycol are used to selectively precipitate LDL and VLDL. The cholesterol in the supernatent after centrifugation is measured enzymatically and corresponds to HDL-C. VLDL cholesterol is estimated by the measurement of triglyceride concentration. Triglycerides (TG) are water soluble lipids consisting of fatty acids and glycerol. TG is measured enzymatically after hydrolysis (to release glycerol) and conversion to a dye. The VLDL cholesterol is determined by dividing the TG concentration by 5.

The accurate measurement of LDL cholesterol depends on the separation of LDL particles in serum from other lipoproteins, i.e., VLDL and HDL, prior to the measurement of LDL-C. N. Rifai and R. Warnick, eds., *Lipid and Lipoprotein Risk Factors*, AAAC press, 1991. Clinical measurement of LDL-C is nevertheless currently performed indirectly using the Friedwald method. Friedwald et al., *Clinical Chemistry*, 18:499 (1972). The LDL-C value is estimated by subtracting HDL-C and VLDL-C (TG/5) from total cholesterol (TC). This method thus involves three measurements and an arithmetic calculation.

Separation of LDL from plasma can be performed by preparative ultracentrifugation, a time consuming and cumbersome method. Additionally, size exclusion chromatography (Rudel et al., *Biochemistry Journal*, 139:89 (1974)), HPLC gel filtration (Williams et al., *J. Chromatography*, 375:233 (1986)) and chemical precipitation (Wieland and Seidel, *J. Lipid Res.*, 24:904–909 (1983)) have been used as alternative separation methods. Chromatography has remained a time consuming (24 hrs) option, while LDL precipitation is no more reliable than the methods used for HDL quantitation. N. Rifai and R. Warnick, eds., *Lipid and Lipoprotein Risk Factors*, AAAC press, 1991.

The prevalent Friedwald method has several limitations. Three measurements must be made, usually involving different instruments, reagents, controls and error profiles. Subtraction of 3 values introduces errors which are additive. Furthermore, the relative error of the total cholesterol measurements affects the error in LDL estimation differently depending on the LDL-C/TC ratio. Using the Friedwald method, the patient's TC concentration must be less than 400 mg/dL, and less than 200 mg/dL for high accuracy, and chylomicrons should not be present. The plasma must be from a fasting patient, since TG levels, which are involved in the calculation, are raised for 6 hours after a meal involving consumption of fat. In addition, patients with type III hyperlipoproteinemia have abnormal VLDL (more cholesterol relative to TG) and cannot be accurately estimated.

The Friedwald method has been found to provide estimated LDL-C values within 10% of ultracentrifugation measurements in 90% of measurements (where TC<200 mg/dL). Warnick et al., *Clinical Chemistry*, 36:15 (1990). For TC levels between 200–400 mg/dL, the LDL-C values fall within 10% of ultracentrifuge measurements in 72% of measurements, while above 400 mg/dL the figure drops to 39%.

The NCEP cut-off LDL standards of 130 and 160 mg/dL were based on Friedwald-type measurements. Accordingly, since the "LDL" estimated by precipitation also includes Intermediate Density Lipoprotein (IDL), the cut-off standards based on epidemiological data may not apply to directly measured LDL values.

An immunological measurement of apo-B, the major protein component of LDL has been developed. Albers et al., *J. Lipid Research*, 30:1445 (1989). While potentially useful in profiling atherogenic potential, this assay is complementary and not a substitute for direct LDL-C measurement. Another approach involves direct profiling of all lipoproteins by 1H-NMR spectroscopy. Otvas et al., (Abstract) AACC Annual Meeting, Washington, D.C., July 1991.

SUMMARY OF THE INVENTION

The invention provides methods for the rapid quantitative determination of low density lipoprotein (LDL) in a biological fluid sample containing LDL, very low density lipoprotein (VLDL) and high density lipoprotein (HDL). In the method of the invention, the sample is passed through a matrix, e.g., a chromatography matrix or capillary, to bind LDL to the matrix. The LDL then is eluted from the matrix differentially from VLDL and HDL. A parameter representative of the concentration of a solute exiting the matrix during an interval when LDL is eluted is then determined, wherein the parameter is proportional to the amount of the LDL in the sample. The parameter may be determined, e.g., by electronically integrating under a detected peak of eluted LDL, obtained, e.g., utilizing a spectrophotometer, or by conducting an enzymatic determination of separated LDL using methods known per se. In one embodiment, the parameter representing the concentration of LDL is compared to a standard. Based on the determination of LDL, the LDL-C content also may be determined.

The matrix may comprise an ion exchange column, such as a cation exchange column. In one preferred embodiment, the matrix may comprise a perfusive cation exchange chromatography matrix, which permits the concentration of LDL to be determined rapidly, e.g., in less than 10 minutes, typically less than 3 minutes. Perfusive chromatography matrices are disclosed in U.S. Pat. No. 5,019,270, issued May 28, 1991, the disclosure of which is incorporated herein by reference. Perfusive chromatography matrices are designed to operate efficiently at exceptionally high flow rates. Perfusive matrices define first and second interconnected sets of pores and a high surface area for solute interaction in fluid communication with the members of the second set of pores. The first and second sets of pores are embodied, for example, as the interstices among particles and throughpores within the particles. The pores are dimensioned such that, at achievable high fluid flow rates, convective flow occurs in both pore sets, and the convective flow rate exceeds the rate of solute diffusion in the second pore set. This technology overcomes the constraint of diffusive mass transport to and from the active surface, and permits increases in fluid velocity without band spreading. In one embodiment, the perfusive matrix is adjusted to a pH less than 7, e.g., pH 6.2.

The methods for the separation and quantification of LDL disclosed herein provide several operational advantages over the existing techniques involving precipitation. The methods for the measurement of LDL disclosed herein are direct and very fast (e.g., less than 10 minutes, typically less than 3 minutes). Furthermore, patient fasting is not required since VLDL is physically separated and does not interfere with the measurement. Because the measurement is direct, the usual error propagation in subtracting three distinct measurements, using the Friedwald method, is avoided. Finally, with the availability of automated HPLC instruments, the assay of the invention is readily automated with little operator involvement. The assay also provides increased accuracy and reliability since neither pipetting of reagents nor dilution are required.

DETAILED DESCRIPTION

The invention provides methods for the rapid quantitative determination of low density lipoprotein (LDL) in a biological fluid sample containing LDL, very low density lipoprotein (VLDL) and high density lipoprotein (HDL). The sample first is passed through a matrix to bind LDL to the matrix. The matrix may comprise, e.g., a chromatography matrix or a capillary. The LDL is then eluted from the matrix differentially from VLDL and HDL. Subsequently, a parameter representative of the concentration of a solute exiting the matrix during an interval when LDL is eluted is determined. The parameter is proportional to the amount of the LDL in the sample. The parameter may be determined, e.g., by electronically or otherwise integrating under a detected peak of eluted LDL. The peak of LDL may be detected, e.g., spectrophotometrically. The amount of LDL-C also may be determined based on the determined amount of LDL. In one embodiment, the concentration of the separated LDL may be determined by conducting an enzymatic assay using methods known per se.

In one embodiment, the matrix may comprise an ion exchange column, such as a cation exchange column. In another embodiment, the matrix may comprise immobilized heparin. The matrix may comprise, e.g., a perfusive chromatography matrix with heparin immobilized on the matrix. In a preferred embodiment, LDL in a plasma sample can be measured using a cation exchange perfusive chromatography matrix. The use of a perfusive matrix permits the rapid determination of LDL (e.g., in less than 10 minutes, typically less than three minutes). Perfusive chromatography matrices are disclosed in U.S. Pat. No. 5,019,270, issued May 28, 1991, the disclosure of which is incorporated herein by reference. Perfusive chromatography matrices are available from PerSeptive Biosystems, Cambridge, Mass, under the trade name Perfusion Chromatography ™ matrices. Perfusive chromatography matrices are designed for operation at exceptionally high flow rates. Perfusive matrices define first and second interconnected sets of pores and a high surface area for solute interaction in fluid communication with the members of the second set of pores. The first and second sets of pores are embodied, for example, as the interstices among particles and throughpores within the particles. The pores are dimensioned such that, at achievable high fluid flow rates, convective flow occurs in both pore sets, and the convective flow rate exceeds the rate of solute diffusion in the second pore set. This technology overcomes the constraint of diffusive mass transport to and from the active surface, and permits increases in fluid velocity without band spreading.

Figure 1:
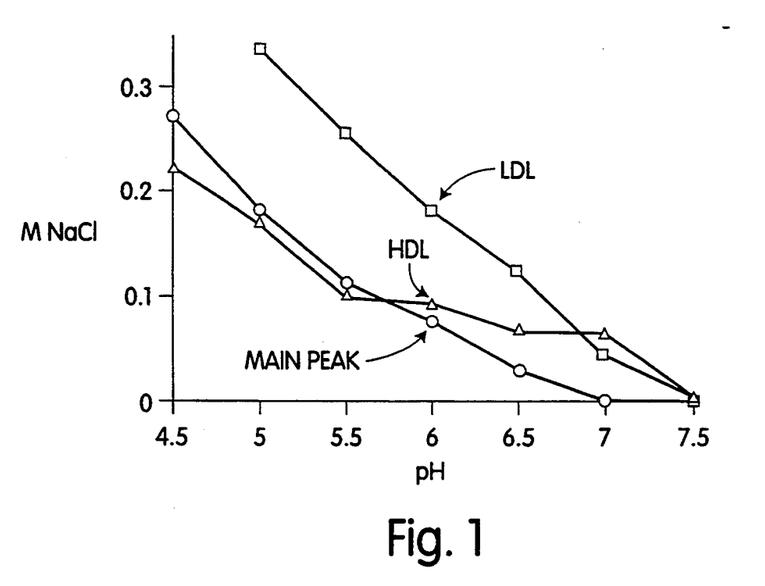
FIG. 1 is a graph illustrating the separation of LDL from HDL and other plasma proteins from a plasma sample using a linear gradient of NaCl and different buffer pH values ranging from 4.5 to 7.5.

In one embodiment of the invention, the chromatography matrix may comprise a POROS HS/M 4.6×100 mm column (Perseptive Biosystems Inc., Cambridge, Mass.), a strong cation exchange perfusive chromatography column, which may be utilized conveniently and rapidly to determine the amount of LDL in a plasma sample. In this embodiment, a pH below 7 is preferred. Optimal separation of LDL may be implemented, e.g., at pH 6.2. FIG. 1 is a graph comparing the separation of LDL and HDL from a plasma sample at 0.5 pH unit increments between pH 4.5 and 7.5 using a linear gradient of NaCl on the perfusive POROS HS/M column. Below pH 7 a clear separation of LDL from HDL and other plasma proteins is obtained.

Table 1 summarizes a set of preferred chromatographic conditions which may be utilized to separate LDL from HDL and other proteins in a plasma sample, and subsequently to permit determination of the quantity of LDL in the plasma sample. Alternative choices of column, column dimension, particle size, pH, gradient, integration method and run time are possible within the scope of the invention which will be apparent to those skilled in the art in view of the disclosure herein.

TABLE 1

| Column: | POROS HS/M 4.6 × 100 |
|---|---|
| Flow Rate: | 5 ml/min |
| Buffer A: | 20 mm MES* pH 6.2 |
| Buffer B: | 20 mm MES* pH 6.2 + 1 M NaCl |
| Gradient: | 0 to 100% in 5 minutes or |
|  | 0 to 60% in 3 minutes |
| Detector: | UV or Diode Array at 214 nm. |

*2-[N-Morpholino]ethanesulfonic acid

Figure 2:
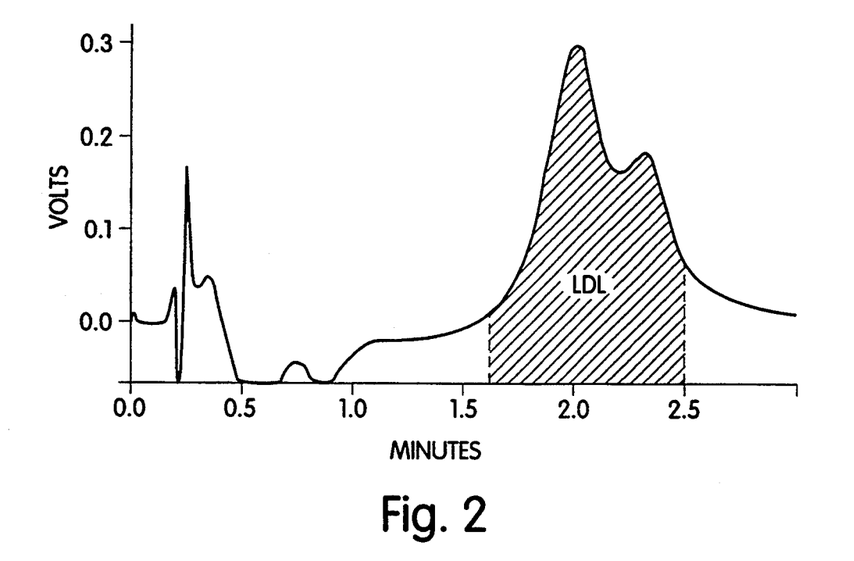
FIG. 2 is a chromatogram of an LDL standard obtained by preparative precipitation and size exclusion chromatography.
Figure 3:
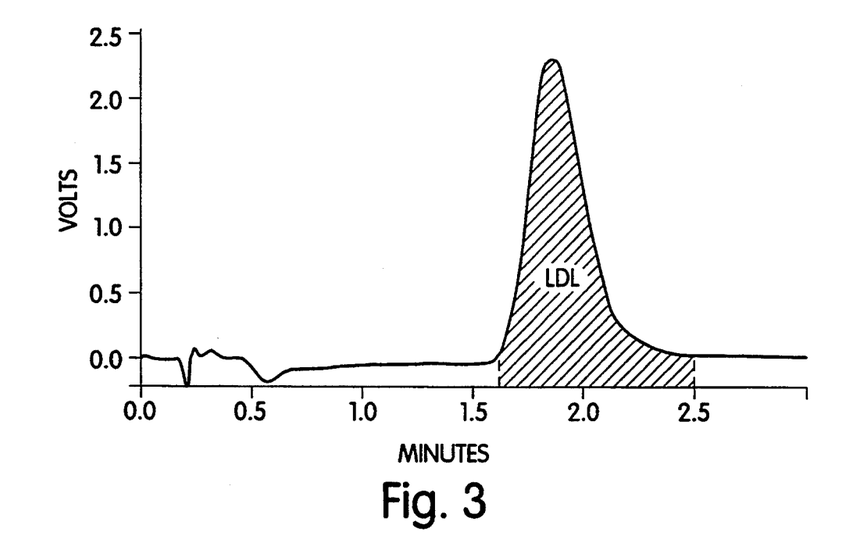
FIG. 3 is a chromatogram of LDL purified by ultracentrifugation.

The conditions of Table 1 were utilized to isolate LDL from a series of samples, in chromatography runs utilizing a semi automated system (SSI-PA, Scientific Systems Inc., State College, Pa.) with manual injection. FIG. 2 is a chromatogram of an LDL standard (Sigma, St. Louis, Mo.) obtained by preparative precipitation and size exclusion chromatography. The peak of LDL elutes between 1.6 and 2.5 minutes. FIG. 3 is a chromatogram showing the profile of LDL from a more homogeneous preparation of LDL purified by ultracentrifugation.

Figure 4:
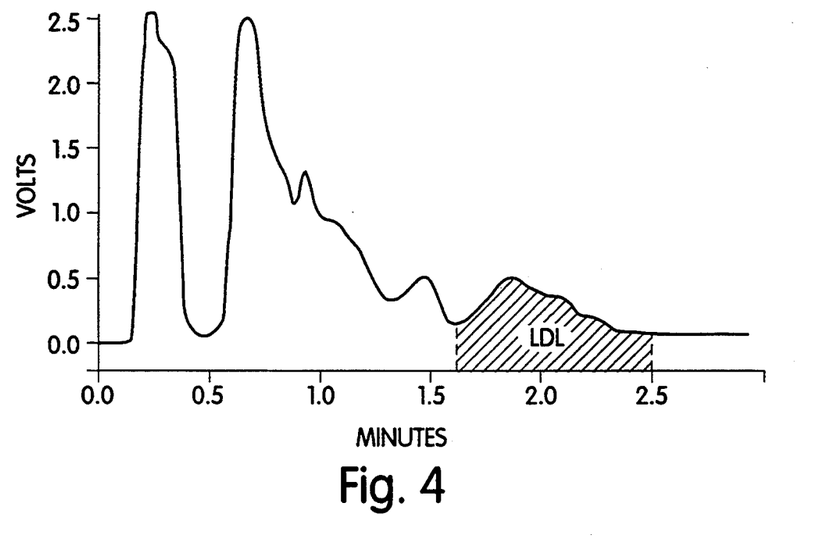
FIGS. 4–7 are chromatograms of human plasma samples.

FIG. 4 shows an analytical chromatogram of a human plasma sample (20 $\mu$l injection). The peak between 1.6 and 2.5 minutes corresponds to LDL. The peak of LDL after 1.5 minutes consists of several distinct but partially overlapped component peaks, which may be attributable to either surface charge heterogeneity, leading to elution at different points along the salt gradient, or to size exclusion effects. Size exclusion or ultracentrifugation size gradients have revealed several subspecies of LDL differing in size. McNamara et al., Arteriosclerosis, 7:483 (1987). The POROS HS/M may act at one level as a wide pore size exclusion column separating the LDL subfractions.

The area of the peak in the chromatogram corresponding to LDL between 1.6 and 2.5 minutes is obtained by electronic integration. The area of the peak may be correlated with the LDL-C concentration. UV absorbance primarily measures protein content. However, the area of the absorbance peak corresponding to LDL also provides a measurement of the LDL cholesterol (LDL-C), since the cholesterol content of LDL is proportional to the protein content. On an average weight basis, LDL comprises 38% cholesterol ester, 8% unesterified cholesterol, and 21% protein. Chapman, J. Methods in Enzymology, 128:70 (1986).

Figure 5:
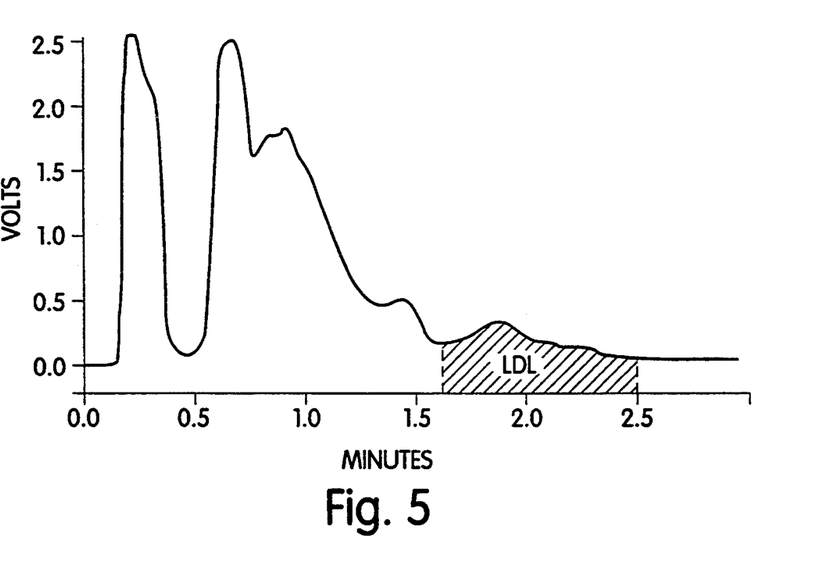
Figure 6:
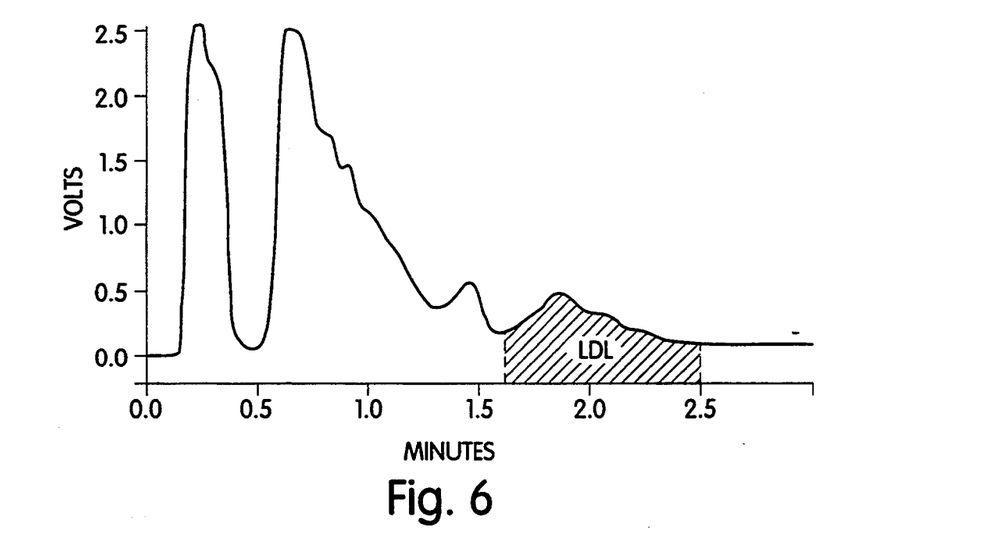
Figure 7:
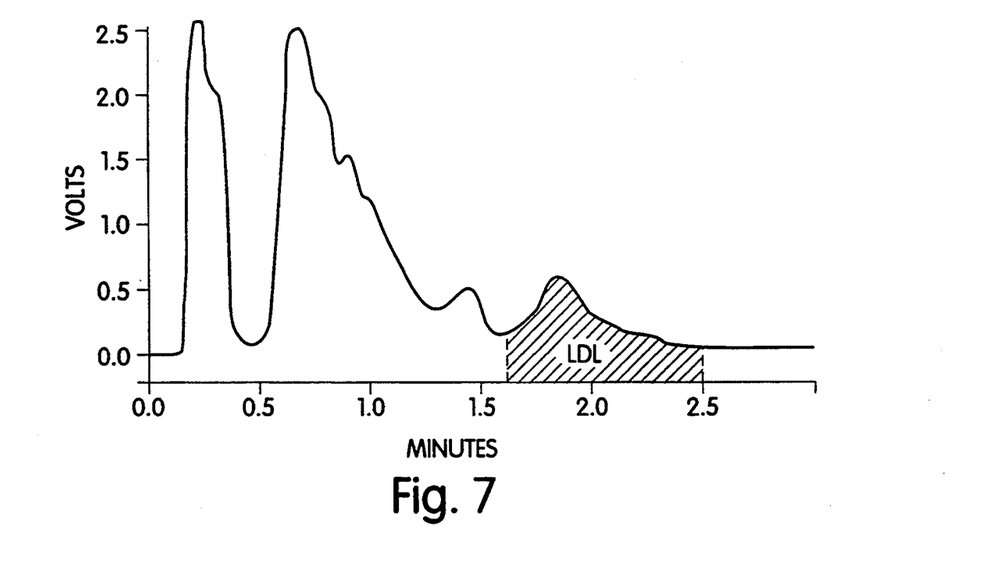

FIGS. 5 through 7 are chromatograms of three additional patient plasma samples, which were stored for more than 7 days under refrigeration. The peak between 1.6 and 2.5 minutes corresponds to LDL. The area (in arbitrary units) of the peak corresponding to LDL in each of the plasma samples in FIGS. 4–7 was determined by electronic integration. The LDL-C for these samples was also determined clinically using the Friedwald method. Table 2 summarizes the correspondence between the integrated areas of each LDL peak with the clinical measurements (Friedwald) of LDL-C for these patient samples.

TABLE 2

| Figure | LDL-C (mg/dL) Friedwald | Area (Millions) |
|---|---|---|
| 4 | 140 | 8.46 |
| 5 | 81 | 4.5 |
| 6 | 110 | 6.64 |
| 7 | 157 | 7.59 |

Figure 8:
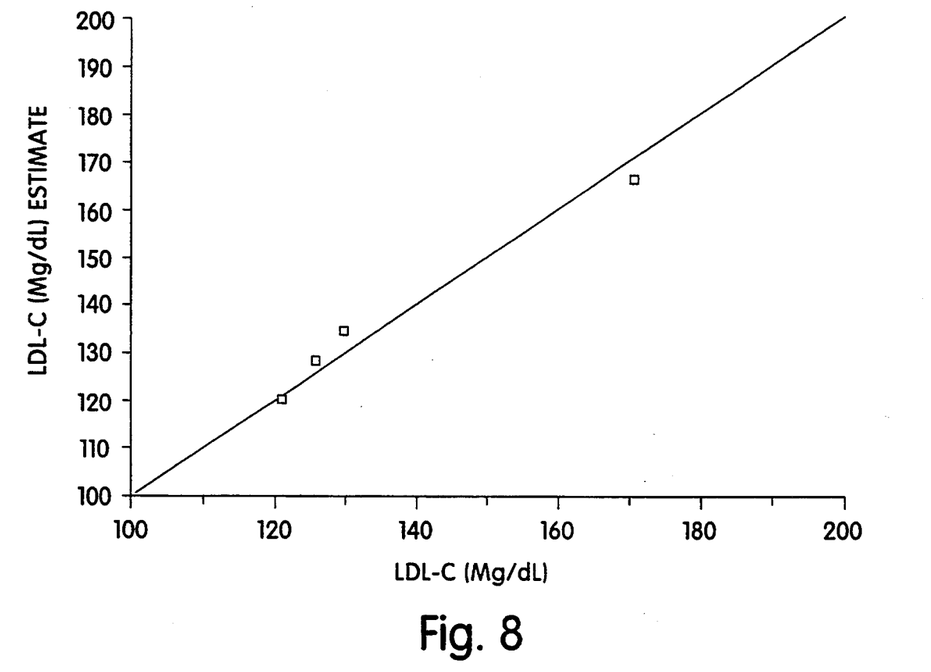
FIG. 8 is a graph illustrating the correlation of the empirically predicted values of LDL-C with the clinically measured (Friedwald) LDL-C values for the plasma samples of Table 3.

Chromatograms of a second set of fresh plasma samples were obtained using the perfusive cation exchange chromatographic conditions of Table 1. 20 microliter injections were used for the four samples. For each sample, the area of the peak of the chromatogram corresponding to LDL was obtained by electronic integration. Table 3 lists the areas of the LDL peaks obtained as well as the corresponding values of LDL-C obtained clinically for these samples. A regression coefficient of 0.97 was obtained for the data of Table 3. FIG. 8 is a graph showing the correspondence of the clinically measured values of LDL-C with the predicted values of LDL-C, for the data of Table 3. The predicted value of LDL-C is obtained based on the area using the empirical correlation from the data of Table 3 (predicted LDL-C (mg/dL)=20.04 (Area×$10^6$)).

TABLE 3

| LDL-C (mg/dL) Friedwald | Area (millions) |
|---|---|
| 121 | 6.0 |
| 126 | 6.4 |
| 171 | 8.3 |
| 130 | 6.7 |

Regression Coefficient = 0.97
LDL-C (mg/dL) = 20.04 (Area × $10^{-6}$)

Figure 9:
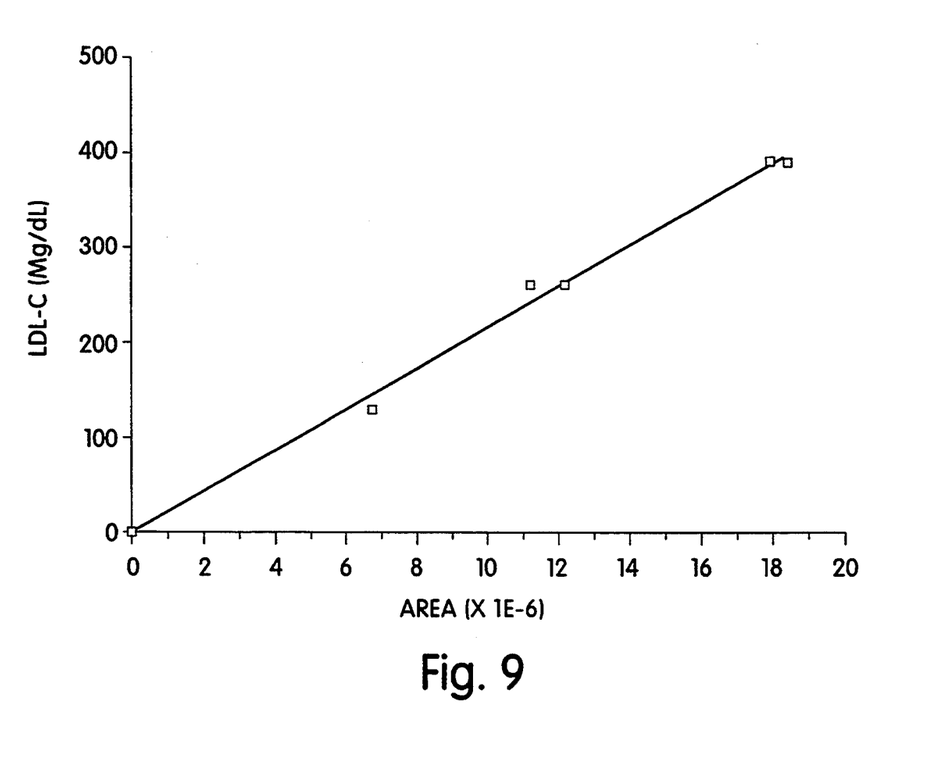
FIG. 9 is a graph illustrating the correspondence of the integrated area of the peak corresponding to LDL with the clinically measured (Friedwald) LDL-C values for the data of Table 4.

Additionally, a calibration plot was obtained by chromatographically analyzing 40 and 80 microliter injections of the 130 mg/dL sample of Table 3. The calibration data is summarized in Table 4. A regression coefficient of 0.99 is obtained. The constant (21.61) differs by 8% from that obtained empirically from the samples of Table 3 (20.04). FIG. 9 is a graph showing the data of Table 4 and the line of best fit.

TABLE 4

| LDL-C (mg/dL) Friedwald | Area (millions) | Injection Volume (µl) |
|---|---|---|
| 130 | 6.7 | 20 |
| 260 | 11.2 | 40 |
| 260 | 12.1 | 40 |
| 390 | 17.9 | 80 |
| 390 | 18.4 | 80 |

Regression Coefficient = 0.99
LDL-C (mg/dL) = 21.61 (Area × $10^{-6}$)

Figure 10:
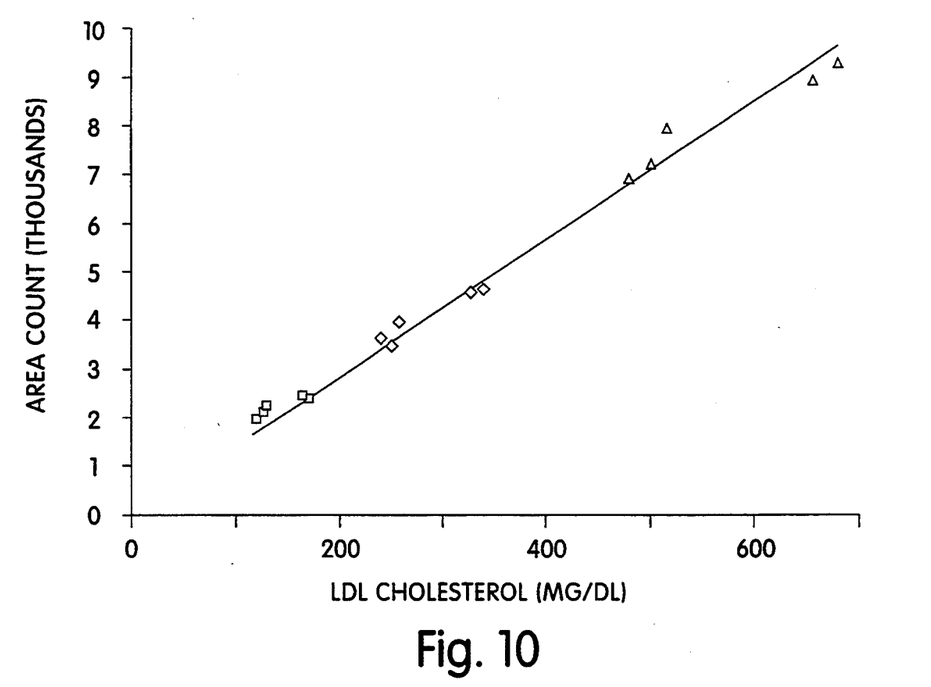
FIG. 10 is a graph illustrating the correlation between the integrated area of the peak of LDL and the clinically measured (Friedwald) LDL-C values for the samples of Table 5.
Figure 11:
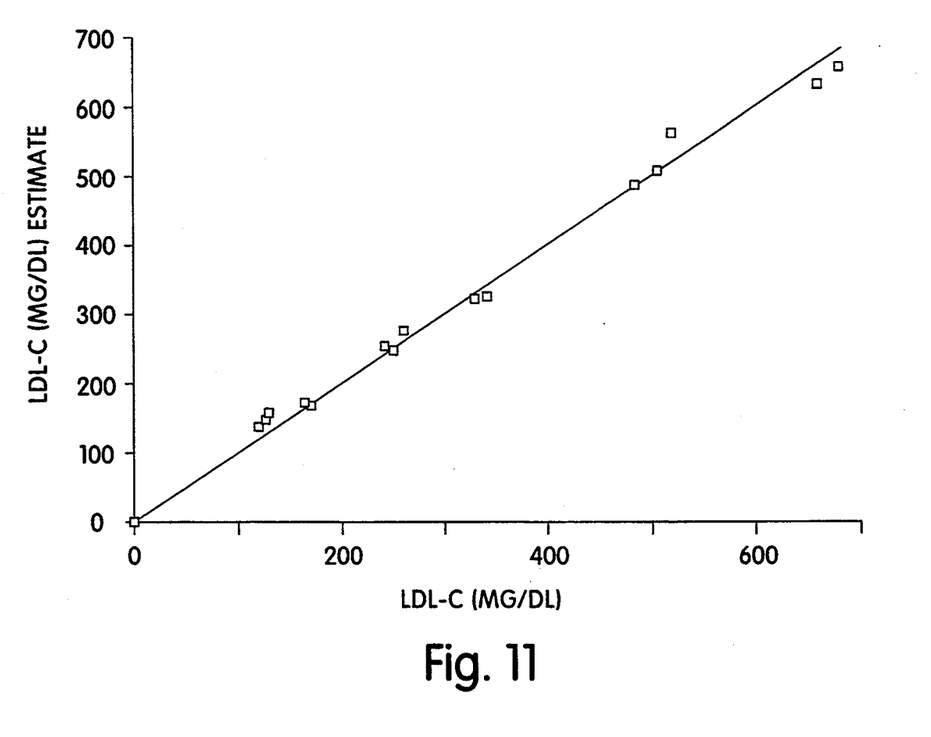
FIG. 11 is a graph illustrating the correlation of the clinically measured (Friedwald) LDL-C values with the empirically predicted values of LDL-C for the samples of Table 5.

The experiments described above were reanalyzed using a HP 1090 automated analytical system (Hewlett Packard, Avondale, Pa.), and the chromatography system of Table 1. Each experiment was performed with 5, 10 and 20 microliter injections (Table 5). FIG. 10 is a graph showing the correlation between the integrated area of the LDL peak and the clinically measured (Friedwald) value of LDL-C for the data of Table 5. The graph also includes a best fit regression line. FIG. 11 is a graph illustrating the predicted LDL-C value based on the empirical constant (0.0707×Area) correlated with the clinically measured (Friedwald) LDL-C values, for the samples of Table 5. In FIGS. 10 and 11, the points below 200 mg/dL represent the 5 µl injections, the points between 200 and 400 mg/dL represent the 10 µl injections, and the points after 400 mg/dL represent the 20 µl injections.

TABLE 5

| LDL-C (mg/dL) Friedwald | Area (Injections) | | |
|---|---|---|---|
| | 5 µl | 10 µl | 20 µl |
| 121 | 1940 | 3576 | 6891 |
| 126 | 2084 | 3432 | 7190 |
| 130 | 2225 | 3914 | 7963 |
| 165 | 2438 | 4538 | 8934 |
| 171 | 2390 | 4590 | 9251 |

Regression Coefficient = 0.99
LDL-C (mg/dL) = 0.0707 (Area)

Figure 12:
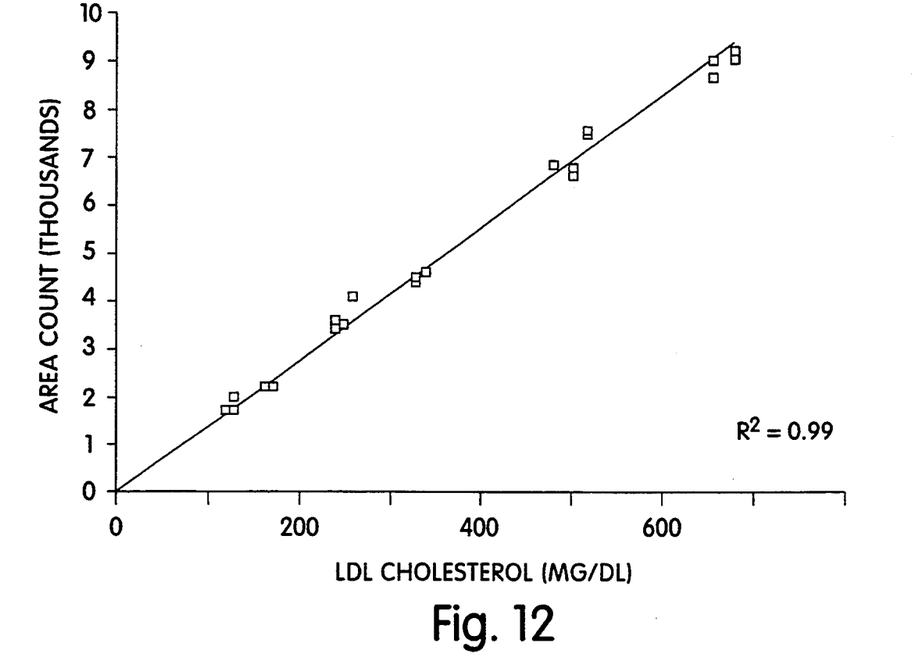
FIG. 12 is a graph illustrating the correlation between the integrated area of the peak of LDL and the clinically measured (Friedwald) LDL-C of the samples of Table 6.

In order to assess the reproducibility of this technique, the samples were run in duplicate a second time (Table 6). FIG. 12 is a graph showing the correspondence between the integrated area of the LDL peak and the clinically measured (Friedwald) LDL-C value for the data of Table 6. A regression coefficient of 0.99 is obtained.

TABLE 6

| LDL-C (mg/dL) Friedwald | Area (Injections) | | |
|---|---|---|---|
| | 5 µl | 10 µl | 20 µl |
| 121 | 1729 | 3421 | 6749 |
| | 1720 | 3556 | 6721 |
| 126 | 1750 | 3468 | 6511 |
| | 1747 | 3493 | 6722 |
| 130 | 2001 | 4021 | 7385 |
| | 1996 | 4062 | 7467 |
| 165 | 2228 | 4355 | 8890 |
| | 2226 | 4459 | 8536 |
| 171 | 2232 | 4570 | 9055 |
| | 2264 | 4526 | 8914 |

Regression Coefficient = 0.99
LDL-C (mg/dL) = 0.0731 (Area)

Figure 13:
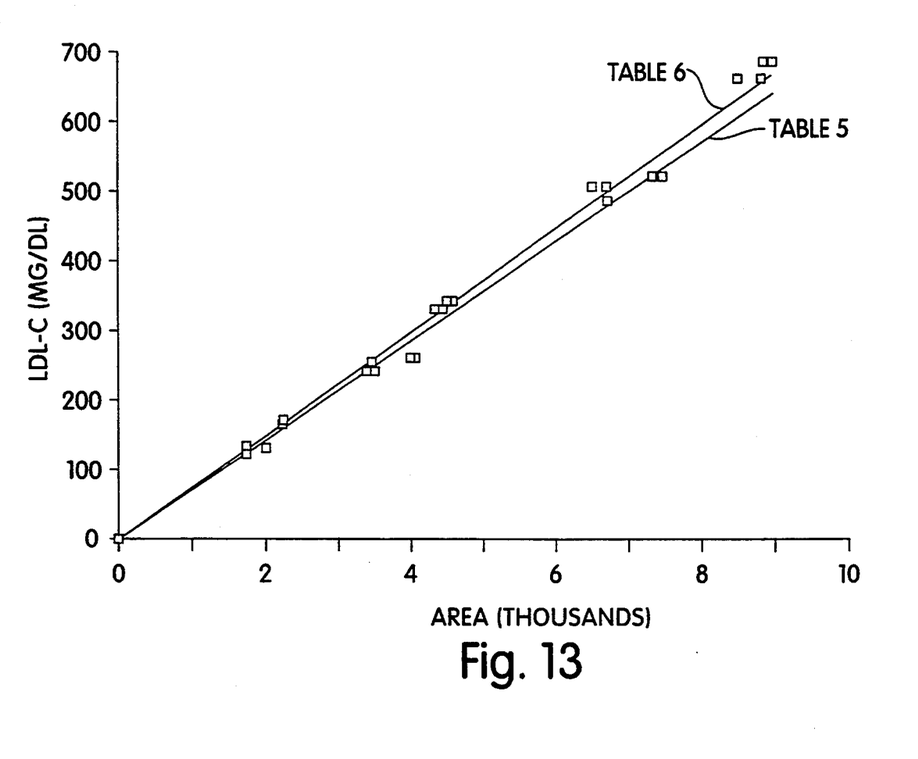
FIG. 13 is a graph illustrating the correlation between the clinically measured (Friedwald) LDL-C and the integrated area of the peak of LDL for the samples in Table 6 along the best fit lines obtained using the data of Tables 5 and 6.
Figure 14:
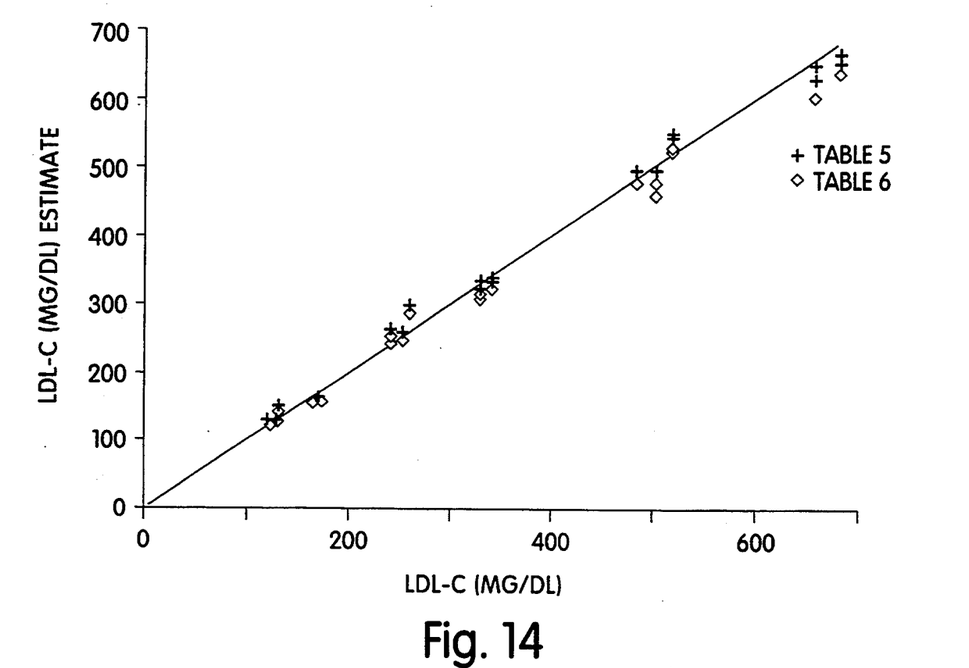
FIG. 14 is a graph illustrating the correlation between the clinically measured (Friedwald) values of LDL-C and the values of LDL-C empirically predicted using the data of Tables 5 and 6.
Figure 15:
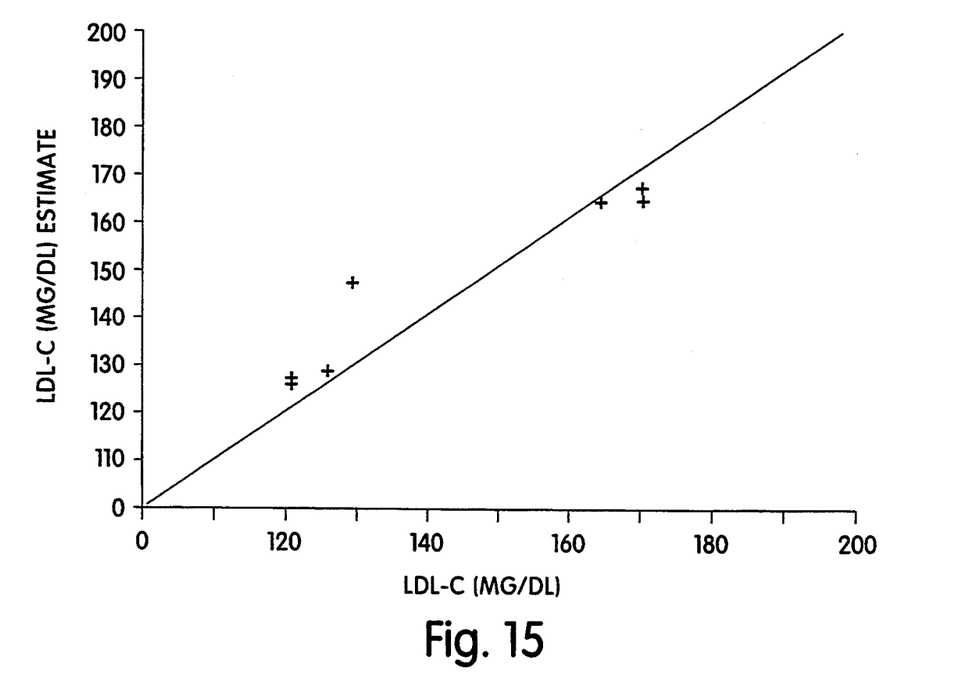
FIG. 15 is a graph illustrating the correlation of the clinically measured LDL-C value with the value predicted empirically, using the data of Table 6, in the clinically relevant regime.
Figure 16:
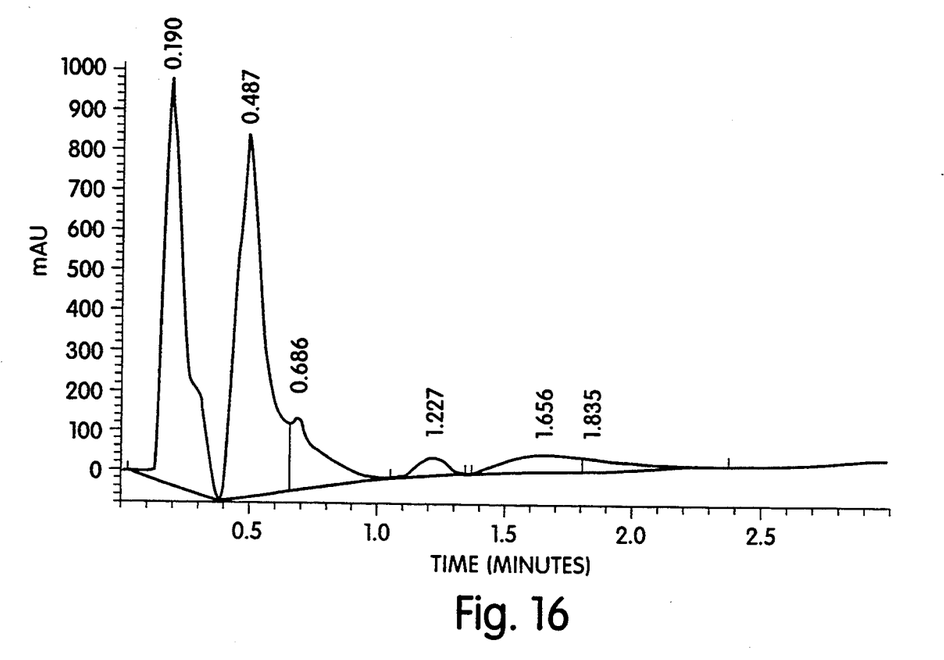
FIGS. 16 and 17 are chromatograms showing elution profiles of LDL from a plasma sample respectively before and after precipitation with heparin.
Figure 17:
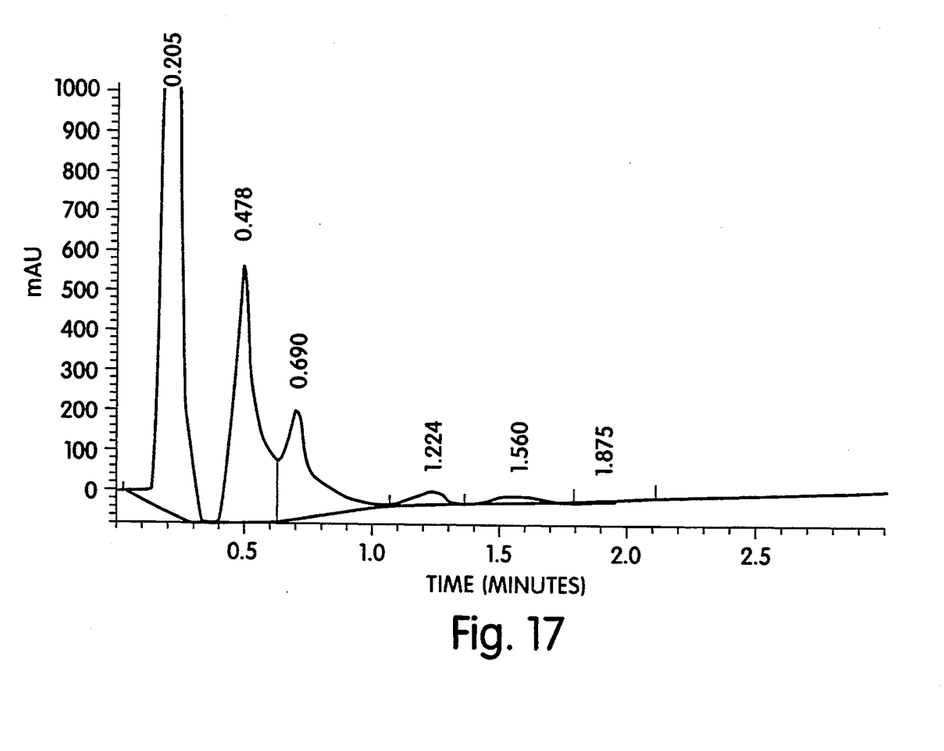

FIG. 13 is a graph showing the correlation between the data in Table 6 and the bet fit line obtained from the data in Tables 5 and 6 respectively. The two regressions provide estimates within 3% of each other. FIG. 14 is a graph correlating clinically measured (Friedwald) LDL-C values with LDL-C values predicted using the empirical correlation using the data from Tables 5 and 6. FIG. 15 is a graph correlating the clinically measured LDL-C values with those predicted empirically using the data of Table 6, in the clinically relevant regime, between 100–200 mg/dL. As additional evidence of the identity of the last peak, a specific precipitation of LDL was implemented followed by chromatography. FIGS. 16 and 17 respectively show an elution profile of a plasma sample before and after reduction of the last peak (LDL) by precipitation with heparin. Reduction of some of the other proteins also occurs, because heparin, the precipitating agent, binds to some of the other proteins as well.

The methods for the separation and quantification of LDL disclosed herein provide several advantages over the existing techniques. The methods disclosed herein are direct and very fast (e.g., less than 10 minutes, typically less than 3 minutes) and are readily automated with little operator involvement. Furthermore, patient fasting is not required since VLDL is physically separated and does not interfere with the measurement. The accuracy of the assay of the invention is enhanced because neither the dilution of a sample nor the addition of enzymatic or other reagents is required.

It will be understood that the above descriptions are made by way of illustration, and that the invention may take other forms within the spirit of the structures and methods described herein. Variations and modifications will occur to those skilled in the art, and all such variations and modifications are considered to be a part of the invention as defined in the claims.

What is claimed is:

1. A direct method for rapid quantitative determination of low density lipoprotein (LDL) cholesterol in a biological fluid sample containing LDL, very low density lipoprotein (VLDL), and high density lipoprotein (HDL), the method comprising the steps of:
   (a) flowing a said sample through an adsorption chromatography matrix defining solute interactive sites, to convectively transport LDL in said sample to said sites and to bind LDL thereto;
   (b) flowing an eluent through the matrix to elute the LDL differentially from VLDL and HDL;
   (c) obtaining a parameter representative of the concentration of a solute exiting the matrix in step (b) during an interval when LDL is eluted from the matrix, said parameter being proportional to the amount of LDL in said sample; and
   (d) determining the LDL cholesterol content of said sample based on the parameter obtained in step (c);
   wherein steps (a) and (b) are completed in less than ten minutes.

2. The method of claim 1, wherein said matrix is an ion exchange column.

3. The method of claim 2, wherein said matrix is a cation exchange column.

4. The method of claim 1 or 3, wherein said matrix is a perfusive chromatography matrix.

5. The method of claim 4, wherein, prior to step (a), said matrix and said sample are adjusted to a pH less than 7.

6. The method of claim 5, wherein said matrix and sample are adjusted to approximately pH 6.2.

7. The method of claim 1, wherein step (c) is conducted by electronically integrating under a detected peak of eluted LDL.

8. The method of claim 1, wherein step (c) is conducted using a spectrophotometer.

9. The method of claim 1, wherein, in step (d), the parameter is compared to a standard.

10. The method of claim 1 wherein step (a) is conducted in a capillary.

11. The method of claim 1 wherein said matrix comprises immobilized heparin.

12. The method of claim 11 wherein said matrix is a perfusive chromatography matrix.

13. The method of claim 1 wherein said parameter is obtained enzymatically.

14. A direct method for the rapid quantitative determination of low density lipoprotein (LDL) cholesterol in an aqueous biological sample containing LDL, very low density lipoprotein (VLDL) and high density lipoprotein (HDL), the method comprising the steps of:
    (a) flowing a said sample through an adsorption chromatography matrix defining solute interactive sites, to convectively transport LDL in said sample to said sites and to bind LDL thereto;
    (b) flowing an eluent through the matrix to elute the LDL differentially from VLDL and HDL;
    (c) obtaining a parameter representative of the concentration of a solute exiting the matrix in step (b) during an interval when LDL is eluted from the matrix, said parameter being proportional to the amount of LDL in said sample; and
    (d) determining the concentration of LDL cholesterol in the sample by comparison of the parameter obtained in step (c) with a standard.

15. The method of claim 14 wherein the parameter is obtained by electronically integrating under a detected peak of eluted LDL.

* * * * *